(12) United States Patent
Uematsu et al.

(10) Patent No.: US 7,678,567 B2
(45) Date of Patent: Mar. 16, 2010

(54) OPTICAL BIOSENSOR

(75) Inventors: Ikuo Uematsu, Yokohama (JP); Ichiro Tono, Yokohama (JP); Kayoko Oomiya, Yokohama (JP); Hideo Eto, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1002 days.

(21) Appl. No.: 10/899,266

(22) Filed: Jul. 26, 2004

(65) Prior Publication Data

US 2006/0019374 A1    Jan. 26, 2006

(51) Int. Cl.
*C12M 1/34* (2006.01)
*C12M 3/00* (2006.01)
(52) U.S. Cl. .................................. 435/288.7
(58) Field of Classification Search ... 435/287.2–288.7; 385/12; 356/39; 422/82.11
See application file for complete search history.

(56) References Cited

U.S. PATENT DOCUMENTS

| | | | | |
|---|---|---|---|---|
| 5,387,328 | A * | 2/1995 | Sohn | 257/253 |
| 5,547,561 | A * | 8/1996 | Vadgama et al. | 205/793 |
| 5,822,472 | A | 10/1998 | Danielzik et al. | |
| 6,312,961 | B1 | 11/2001 | Voirin et al. | |
| 6,472,163 | B1 * | 10/2002 | Coleman et al. | 435/19 |

FOREIGN PATENT DOCUMENTS

| | | |
|---|---|---|
| JP | 06-186165 | 7/1994 |
| JP | 07-159650 | 6/1995 |
| JP | 08-285851 | 11/1996 |
| JP | 09061346 | 3/1997 |
| JP | 2003-279479 | * 10/2003 |
| JP | 2004085212 | 3/2004 |
| WO | WO 98/21571 | 5/1998 |

OTHER PUBLICATIONS

European Search Report, issued Feb. 22, 2005 in the counterpart European application.
The Patent Office of the State Intellectual Property Office of the People'S Republic of China, "First notice on office action," for Appln. No. 2004100558052,(Dec. 8, 2006).
"Notice of Grounds for Rejection" (re Japanese Patent Application No. 2003-128028), Japanese Patent Office, Jun. 19, 2007.
Japanese Patent Office, "Notice of Grounds for Rejection" (re Japanese Patent Application No. 2003-128028) dated Oct. 16, 2007.

* cited by examiner

*Primary Examiner*—Walter D Griffin
*Assistant Examiner*—Shanta G Doe
(74) *Attorney, Agent, or Firm*—Pillsbury Winthrop Shaw Pittman LLP

(57) ABSTRACT

An optical biosensor has a total reflection plate so as to totally internally reflect and transmit an incident light, a first grating and a second grating disposed separately on the total reflection plate, and a sensing membrane that is containing an enzyme and a chromogenic reagent and is sandwiched by the first and second gratings on the total reflection plate.

13 Claims, 7 Drawing Sheets

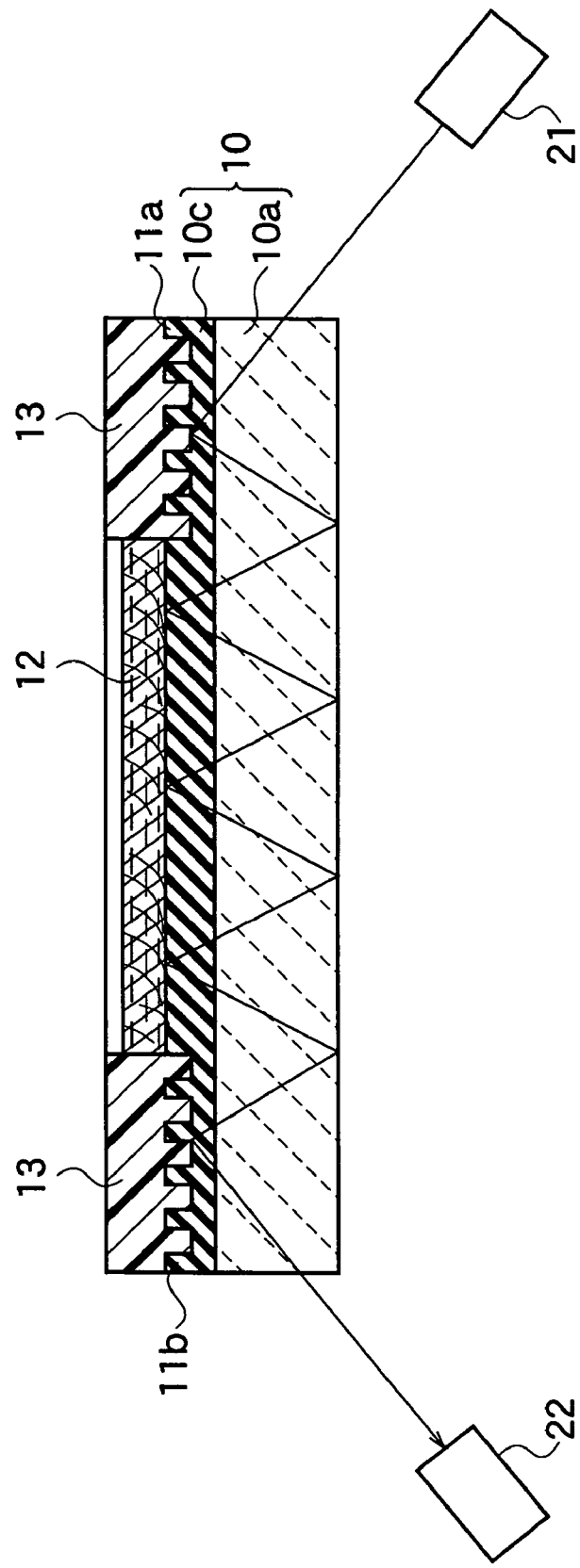

OPTICAL BIOSENSOR

BACKGROUND OF THE INVENTION

1. Field of the Invention

The present invention relates to an apparatus for measuring a specific molecule included in a specimen and in particular to an optical biosensor.

2. Description of the Related Art

A planar lightwave circuit sensor using optical waveguide phenomenon is widely spread as the sensor to measure the amount of the bio molecules existing in body fluid such as blood. As shown in FIG. 1, the planar lightwave circuit has a light source 6, a substrate 1 receiving a light from the light source 6, a first grating 3 delineated on the substrate 1 so as to receive an incident light, a second grating 4 delineated on the substrate 1 so as to diffract the incident light in the direction of the exterior, and the photo detector 7 receiving the diffracted light. Further, the planar lightwave circuit sensor has a single optical waveguide membrane 2 disposed on the substrate 1 so as to transmit the incident light, and a glucose oxidase (GOD) membrane 5 disposed on the optical waveguide membrane 2. The GOD membrane 5 identifies the bio molecules and transforms the information about the amount of the identified bio molecules to a change of an optical intensity.

An existing method for analyzing the bio molecules existing in the blood by the planar lightwave circuit sensor is as follows. At first, the blood is collected from vein with a syringe. The collected blood is dropped on the GOD membrane 5. The laser light is emitted from the light source 6 and diffracted by the first grating 3. The diffracted light penetrates the optical waveguide membrane 2. The evanescent wave is generated at the interface between the optical waveguide membrane 2 and the GOD membrane 5. The intensity of the evanescent wave changes by reaction between the dropped bio molecules contained in the blood and the GOD. The photo detector 7 receives the diffracted light from the second grating 4 and detects the changes of the evanescent wave intensity to analyze the bio molecules contained in the blood as disclosed in Japanese Patent Application Hei9-61346.

However, manufacturing the evanescent wave generates requires precision apparatus and techniques. This is because the incident light reaching at the interface should be diffracted at appropriate angle to measure the change of the evanescent wave intensity precisely.

SUMMARY OF THE INVENTION

An aspect of present invention inheres in an optical biosensor having a total reflection plate so as to totally internally reflect and transmit an incident light, a first grating and a second grating disposed separately on the total reflection plate, and a sensing membrane that is containing an enzyme and a chromogenic reagent and is sandwiched by the first and second gratings on the total reflection plate.

BRIEF DESCRIPTION OF DRAWINGS

FIG. 7 is a cross section of the optical biosensor in accordance with a second modification of the embodiment of the present invention.

DETAILED DESCRIPTION OF THE INVENTION

Figure 1:
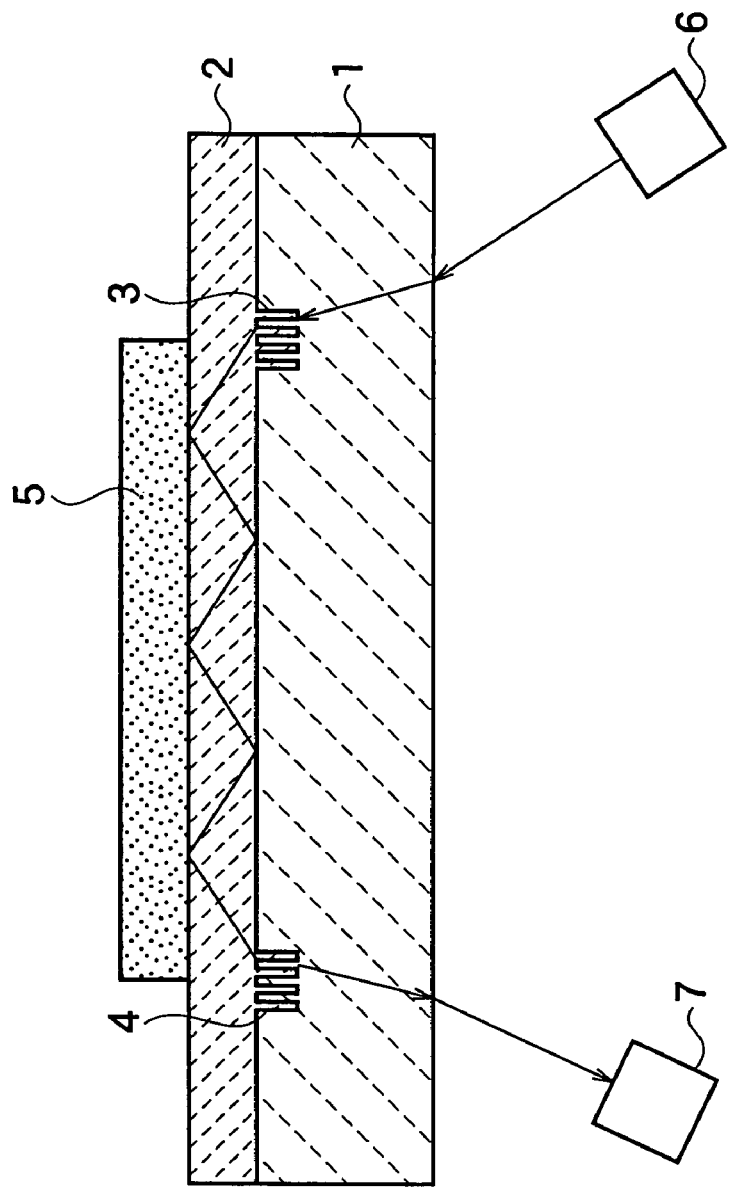
FIG. 1 is a cross section of a planar lightwave circuit sensor.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

Figure 2:
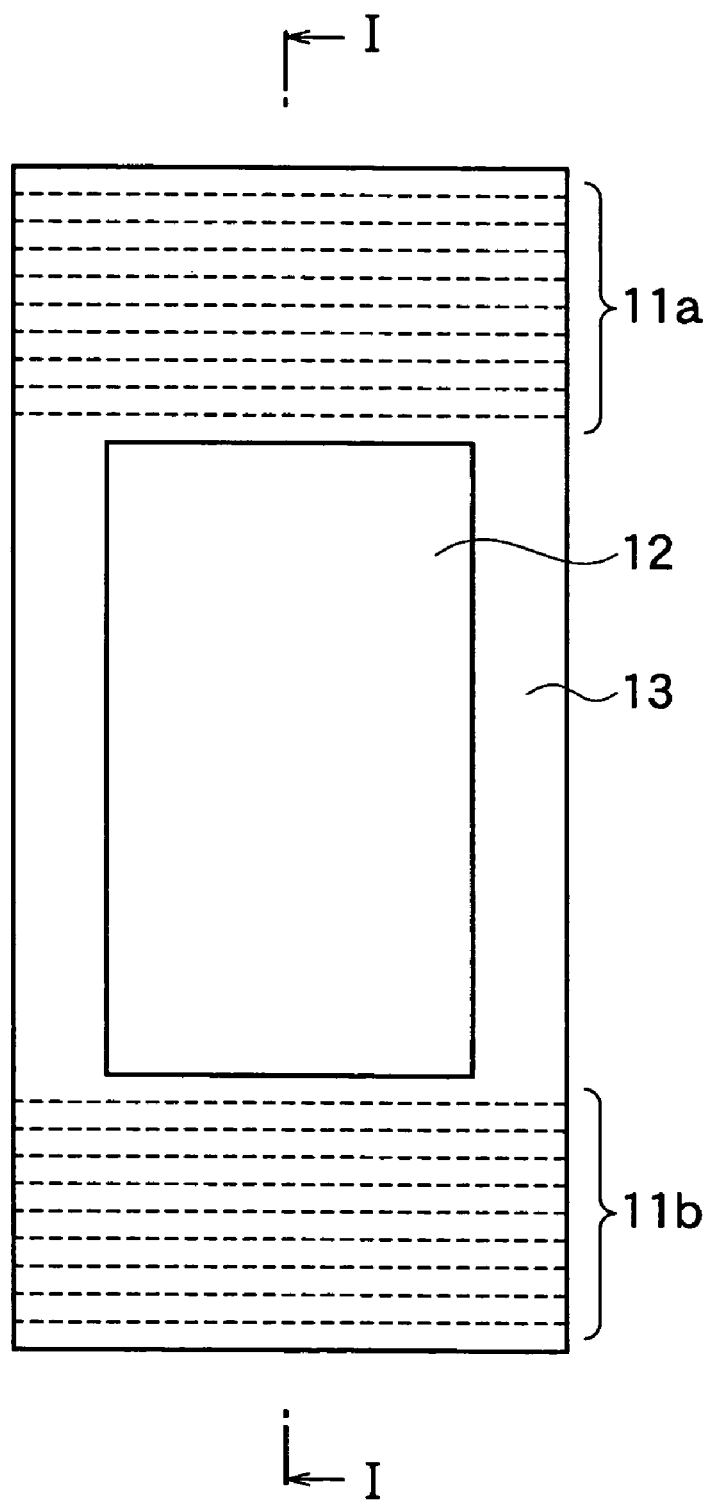
FIG. 2 is a plan view of an optical biosensor in accordance with an embodiment of the present invention.
Figure 3:
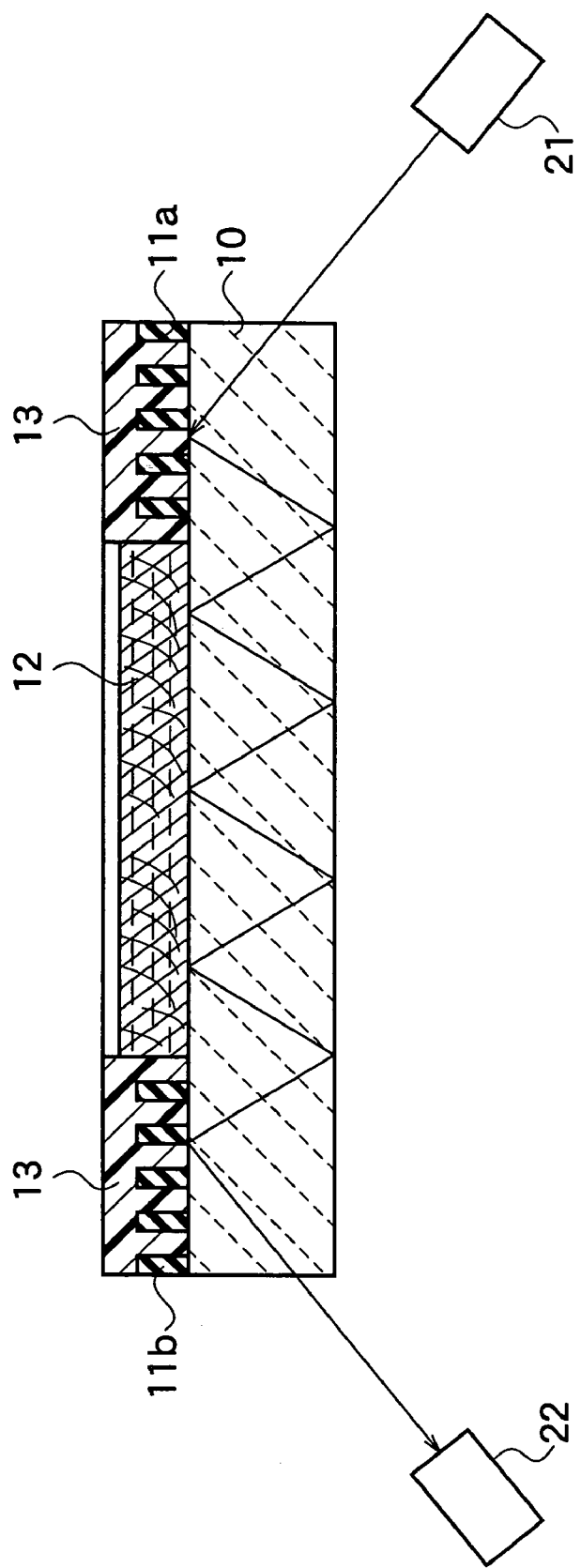
FIG. 3 is a cross section of the optical biosensor in a direction of a line I-I shown in FIG. 2 in accordance with an embodiment of the present invention.

With reference now to FIGS. 2 and 3, an optical biosensor in accordance with an embodiment of the present invention has a total reflection plate 10, a first grating 11a and a second grating 11b on the top surface of the total reflection plate 10, a sensing membrane 12 sandwiched by the first and second gratings 11a, 11b on the top surface of the total reflection plate 10. An incident light is totally internally reflected and transmitted within the total reflection plate 10. The first grating 11a and the second grating 11b are disposed separately on the total reflection plate 10. The sensing membrane 12 contains enzyme and chromogenic reagent. The optical biosensor further has a protection sheet 13 disposed on the top surface of the total reflection plate 10. The protection sheet 13 surrounds the sensing membrane 12 and the protection sheet 13 fits and covers the first and second gratings 11a, 11b.

The total reflection plate 10 is composed of quartz ($SiO_2$), for example. The first and second gratings 11a, 11b are composed of material of which refractive index is higher than the total reflection plate 10. For instance, titanium oxide ($TiO_2$), zinc oxide (ZnO), niobic acid lithium ($LiNbO_3$), gallium arsenide (GaAs), indium tin oxide (ITO), polyimide, or tantalum oxide ($Ta_2O_5$) is deposited on the total reflection plate 10 by chemical vapor deposition (CVD) and selectively etched away with dry etching to form the first and second gratings 11a, 11b.

The sensing membrane 12 is formed by gelation of the enzyme and the chromogenic reagent with cellulose derivative. For example, glucose oxidase (GOD), peroxidase (POD), or mutarotase is useful as the enzyme in the sensing membrane 12 when the biosensor is used for inspecting glucose in a body fluid. 3,3',5,5'-tetramethylbenzidine (TMBZ) is useful for the chromogenic reagent, for example. Reaction formulas (1)-(3) show reactions between the glucose and the enzyme to stain the sensing membrane 12. It should be noted only product related to pigmentation of the sensing membrane 12 is shown in each of reaction formulas (1)-(3).

Glucose+GOD→$H_2O_2$ (1)

$H_2O_2$+POD→Oxygen Radical (O*) (2)

O*+Chromogenic reagent→Pigmentation (3)

The protection sheet 13 is composed of material of which refractive index is lower than the first and second gratings 11a, 11b. Also, it is desirable to use the low refractive index material that does not react with the reagents such as the enzyme and the chromogenic reagent. Coating such low refractive index material on the total reflection plate 10 forms the protection sheet 13.

With reference again to FIG. 3, the incident light emitted by a light source 21 is diffracted by the first grating 11a. The diffracted incident light is totally internally reflected and transmitted within the total reflection plate 10.

When the incident light is refracted at the interface between the total reflection plate 10 and the sensing membrane 12, evanescent wave is absorbed by the pigmentation of the sensing membrane 12. The pigmentation intensity and the absorbed light intensity are in proportion. Also, the pigmentation intensity and the amount of specimen such as the glucose dropped on the sensing membrane 12 are in proportion.

The incident light reaches the second grating 11b and the incident light is diffracted in the direction of a photo detector 22. By detecting the difference between the light intensities emitted by the light source 21 and received by the photo detector 22, it becomes possible to calculate the amount of specimen such as the glucose dropped on the sensing membrane 12.

The optical biosensor in accordance with the embodiment of the present invention employs simplified structure. Therefore, it is possible to manufacture the optical biosensor easily.

(FIRST MODIFICATION)

Figure 4:
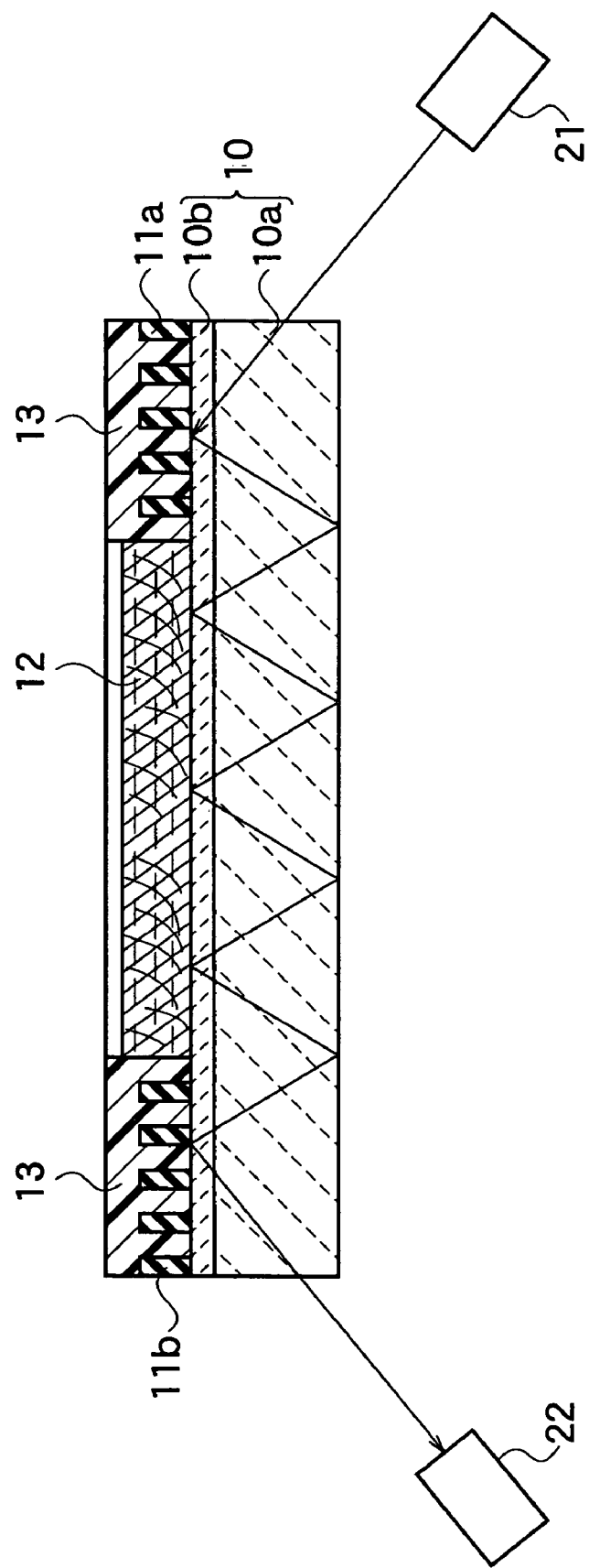
FIG. 4 is a cross section of the optical biosensor in accordance with a first modification of the embodiment of the present invention.

With reference now to FIG. 4, the optical biosensor in accordance with a first modification of the embodiment has the total reflection plate 10 further having a glass plate 10a and a silicon oxide layer 10b disposed on the glass plate 10a. Other elements of the optical biosensor shown in FIG. 4 are similar to the optical biosensor shown in FIG. 3.

Since the quartz is expensive material, the optical biosensor shown in FIG. 4 employs the glass plate 10a and the silicon oxide layer 10b to decrease the manufacturing cost.

The glass plate 10a is composed of non-alkali glass, for example. The silicon oxide layer 10b is formed by depositing silicon oxide ($SiO_2$) on the glass plate 10a by the CVD or the spattering process. Without the silicon oxide layer 10b, heterogeneous metals exist on the glass plate 10a. Therefore, if the sensing membrane 12 is disposed on the glass plate 10a directly, such heterogeneous metals affect preciseness of the inspection.

Figure 5:
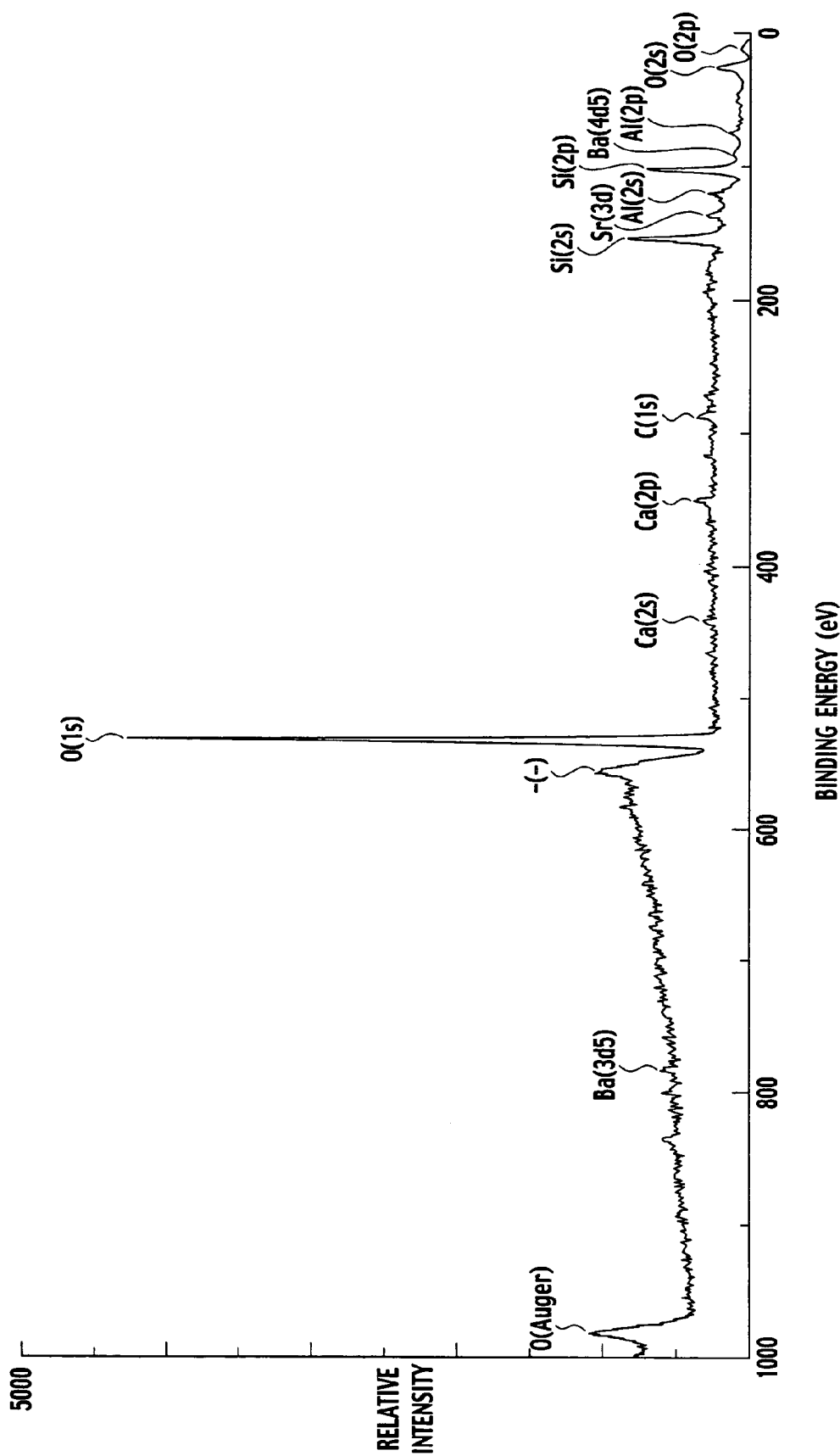
FIG. 5 is a first graph showing relation between binding energy of materials and relative intensity obtained by X-ray photoelectron spectroscopy.
Figure 6:
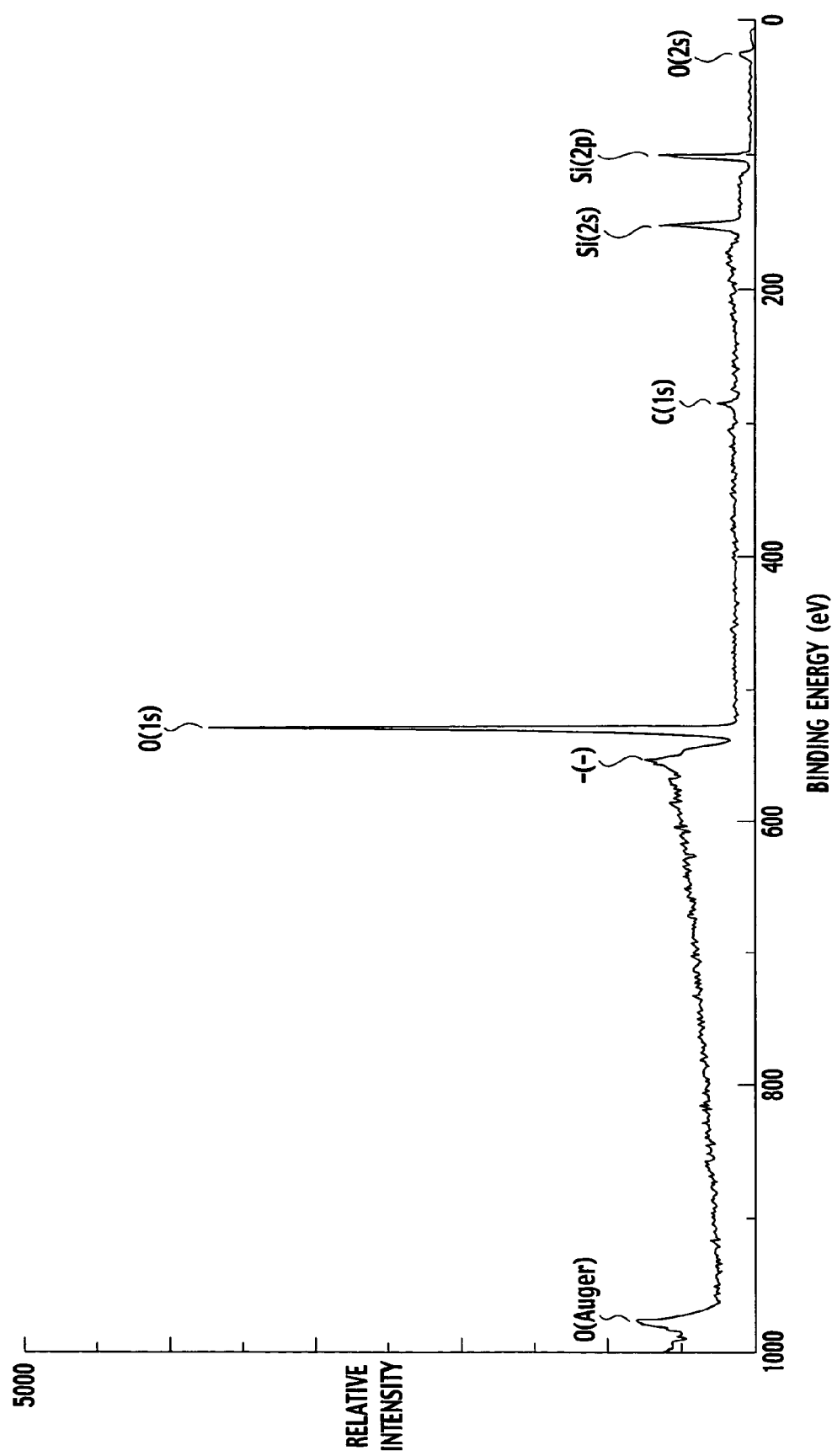
FIG. 6 is a second graph showing relation between binding energy of materials and relative intensity obtained by X-ray photoelectron spectroscopy.

As shown in FIG. 5, the X-ray photoelectron spectroscopy (XPS) reveals that silicon (Si), aluminum (Al), barium (Ba), calcium (Ca), and strontium (Sr) exist on the surface of the glass plate 10a. However, by depositing the silicon oxide layer 10b on the glass plate 10a, only silicon (Si) substantially exists on the surface of the total reflection plate 10 as shown in FIG. 6. Therefore, depositing the silicon oxide layer 10b shown in FIG. 4 eliminates the affect of the heterogeneous metals to the sensing membrane 12. Consequently, it becomes possible to dispose the sensing membrane 12 on the total reflection plate 10 even though the optical biosensor employs the glass plate 10a. As the result, the optical biosensor in accordance with a first modification of the embodiment provides the precise inspection with low manufacturing cost.

(SECOND MODIFICATION)

With reference now to FIG. 7, the optical biosensor in accordance with a second modification of the embodiment has the total reflection plate 10 further having a glass plate 10a and a titanium oxide layer 10c disposed on the glass plate 10a. Other elements of the optical biosensor shown in FIG. 7 are similar to the optical biosensor shown in FIG. 4.

Since the quartz is expensive material as described in the first modification, the optical biosensor shown in FIG. 7 also employs the glass plate 10a and the titanium oxide layer 10c to decrease the manufacturing cost.

The glass plate 10a is composed of non-alkali glass, for example. The titanium oxide layer 10c is formed by depositing titanium oxide ($TiO_2$) on the glass plate 10a by the CVD or the spattering process. The titanium oxide layer 10c has thickness of 180 nm-200 nm, desirably 200 nm so as to maximize the absorbance of the incident light at the interface between the titanium oxide layer 10c and the sensing membrane 12.

After the titanium oxide layer 10c is formed, it is possible to delineate the first and second gratings 11a, 11b easily by selectively etching away the titanium oxide layer 10c with lithography and dry etching techniques.

Further, since the total reflection plate 10 has the glass plate 10a and the titanium oxide layer 10c of which refractive index is higher than the refractive index of the glass plate 10a, the electric field intensity of the evanescent wave is gained at the interface between the titanium oxide layer 10c and the sensing membrane 12.

Consequently, the optical biosensor shown in FIG. 7 in accordance with a second modification of the embodiment provides the precise inspection with low manufacturing cost. Further, it is possible to manufacture the optical biosensor shown in FIG. 7 easily.

OTHER EMBODIMENTS

Although the invention has been described above by reference to the embodiment of the present invention, the present invention is not limited to the embodiment so described. Modifications and variations of the embodiment so described will occur to those skilled in the art, in the light of the above teachings. Therefore, the scope of the invention is defined with reference to the following claims.

What is claimed is:

1. An optical biosensor comprising:
   a light source;
   a first grating diffracting an incident light emitted from the light source;
   a total reflection plate interposed between the light source and the first grating, including a glass layer and a silicone oxide layer provided on a surface of the glass layer, so as to totally internally reflect and transmit a diffracted light diffracted by the first grating;
   a second grating diffracting a transmitted light transmitted within the total reflection plate and outputting a diffracted light diffracted by the second grating to the outside of the total reflection plate;
   a light receiving element receiving the diffracted light diffracted by the second grating; and
   a sensing membrane in contact with the silicon oxide layer, that includes an enzyme and a chromogenic reagent and is provided between the first grating and the second grating on the total reflection plate, wherein
   the first grating and the second grating are in contact with the silicon oxide layer of the total reflection plate, and the diffracted light diffracted by the first grating is internally reflected between a bottom of the glass layer and a top surface of the silicon oxide layer.

2. The optical biosensor of claim 1, wherein the first grating and the second grating have a higher refractive index than the total reflection plate.

3. The optical biosensor of claim 1, further including a protection sheet covering the first grating and the second grating.

4. The optical biosensor of claim 1, wherein the enzyme is a glucose oxidase.

5. The optical biosensor of claim 1, wherein the enzyme is a peroxidase.

6. The optical biosensor of claim 1, wherein the enzyme is a mutarotase.

7. The optical biosensor of claim 1, wherein the chromogenic reagent is a 3,3',5,5'-tetramethylbenzidine.

8. The optical biosensor of claim 1, wherein the sensing membrane contains a cellulose derivative.

9. The optical biosensor of claim 1, wherein the silicon oxide layer is disposed to prevent heterogeneous materials from existing on the total reflection plate.

10. An optical biosensor comprising:
    a light source;
    a first grating diffracting an incident light emitted from the light source;
    a total reflection plate interposed between the light source and the first grating including a glass layer and a titanium oxide layer provided on a surface of the glass layer, so as to totally internally reflect and transmit a diffracted light diffracted by the first grating;
    a second grating diffracting a transmitted light transmitted within the total reflection plate and outputting a diffracted light diffracted by the second grating to outside of the total reflection plate;
    a light receiving element receiving the diffracted light diffracted by the second grating; and
    a sensing membrane in contact with the titanium oxide layer, including an enzyme and a chromogenic reagent and being provided between the first grating and the second grating on the total reflection plate, wherein
    the first grating and the second grating are in contact with the titanium oxide layer of the total reflection plate, and the diffracted light diffracted by the first grating is internally reflected between a bottom of the glass layer and a top surface of the titanium oxide layer.

11. The optical biosensor of claim 10, wherein the titanium oxide layer is disposed to prevent heterogeneous materials from existing on the total reflection plate.

12. The optical biosensor of claim 1, wherein a refractive index of the glass layer is equal to a refractive index of the silicon oxide layer.

13. The optical biosensor of claim 10, wherein a refractive index of the glass layer is equal to a refractive index of the titanium oxide layer.

* * * * *